(12) United States Patent
Kast (10) Patent No.: US 8,128,701 B2
(45) Date of Patent: Mar. 6, 2012

(54) IMPLANT FOR USE BETWEEN SPIRAL VERTEBRAE

(75) Inventor: Erich Kast, Pfungen (CH)

(73) Assignee: ULRICH GmbH & Co. KG, Ulm (DE)

( * ) Notice: Subject to any disclaimer, the term of this patent is extended or adjusted under 35 U.S.C. 154(b) by 456 days.

(21) Appl. No.: 12/257,527

(22) Filed: Oct. 24, 2008

(65) Prior Publication Data

US 2010/0106251 A1    Apr. 29, 2010

(51) Int. Cl.
*A61F 2/44*  (2006.01)
(52) U.S. Cl. .................................... 623/17.15
(58) Field of Classification Search .... 623/17.11–17.16; 606/246–249
See application file for complete search history.

(56) References Cited

U.S. PATENT DOCUMENTS

| | | | |
|---|---|---|---|
| 5,236,460 A * | 8/1993 | Barber ...................... | 623/17.15 |
| 5,360,430 A | 11/1994 | Lin ............................ | 606/61 |
| 6,106,557 A | 8/2000 | Robioneck et al. .......... | 623/17 |
| 6,190,413 B1 * | 2/2001 | Sutcliffe ..................... | 623/17.11 |
| 6,682,561 B2 * | 1/2004 | Songer et al. .............. | 623/17.11 |
| 6,752,832 B2 | 6/2004 | Newmann .................. | 623/17.15 |
| 6,899,735 B2 * | 5/2005 | Coates et al. .............. | 623/17.16 |
| 7,674,296 B2 * | 3/2010 | Rhoda et al. ............... | 623/17.15 |
| 2002/0169508 A1 | 11/2002 | Songer et al. ............. | 623/17.11 |
| 2006/0241770 A1 | 10/2006 | Rhoda et al. ............... | 623/17.15 |

FOREIGN PATENT DOCUMENTS

FR    2897770    8/2007

* cited by examiner

*Primary Examiner* — Eduardo C Robert
*Assistant Examiner* — Tara Carter
(74) *Attorney, Agent, or Firm* — Andrew Wilford (57) ABSTRACT

The invention relates to an implant for use between the vertebrae (8) of the spine as a placeholder for vertebrae or vertebrae parts removed from the spine, having a first implant part (2) and a second implant part (3), which can be adjusted against each other in the direction of the coaxial longitudinal axis thereof for changing the length of the implant (1), and having at least one mounting bracket (10) that can be attached to one of the implant parts (2 and 3), and which faces the adjacent vertebra, and partially overlaps the same. The mounting bracket (10) is formed by a vertebra attachment plate (11) and by a base plate (12) comprising a guide rail (13), protruding from the vertebra attachment plate, and serving for the radial adjustment of the mounting bracket (11) as opposed to the one implant part (2 and 3), is wherein a means is associated with the one implant part (2 and 3) for the radial fixation of the base plate (12).

12 Claims, 7 Drawing Sheets

IMPLANT FOR USE BETWEEN SPIRAL VERTEBRAE

FIELD OF THE INVENTION

The invention relates to an implant for implantation between vertebrae of the spine as a placeholder for vertebrae or vertebral parts removed from the spine, having a first implant part and a second implant part that can be moved relative to each other in the direction of their coaxial longitudinal axis for changing the length of the implant and having at least one mounting bracket that can be attached to one of the implant parts and is that directed toward the adjacent vertebra, at least partially overlapping same.

BACKGROUND OF THE INVENTION

Such an implant is known from EP 0 950 388 [U.S. Pat. No. 6,190,413]. This implant is comprised of a total of three implant is parts; two end permanent parts installed on the adjacent vertebra, and one center implant part positioned between them, which are connected to each other via screwthreads. Holes are formed in the end implant parts serving primarily for enabling access to the interior of the implant parts for inserting bone cement or bone material. These holes are also utilized to optionally attach a mounting bracket having a circular collar to one of the end implant parts, holes being formed in the collar that can be aligned with two holes formed in the end implant part. Bolts can be fitted through the aligned holes. The mounting bracket has a longitudinal slot whose width varies such that the pins can be fixed in the holes. As a result the mounting bracket is attached at the outer edge of the end implant part, and can be utilized to improve the stability of the spine without preventing access to the implant parts.

One disadvantage of this known implant, however, is that it is subject to limitation in increasingly used minimal invasive surgery, because in order to change the length of the implant the center implant must be adjusted as opposed to the end implant part by attaching to it a tool that moves in a circular arc, and adjustment to the individual conditions of the patient is not possible due to the arrangement of the mounting bracket on the outer circumference of the end implant part.

OBJECT OF THE INVENTION

The object of the invention is therefore to provide an implant of the type described above in which the position of the mounting bracket can be changed as opposed to the implant.

SUMMARY OF THE INVENTION

This object is attained in an implant of the type described above according to the invention in that the mounting bracket is formed by means of a vertebra attachment plate and a base plate having a guide rail that is positioned at a distance from the vertebra attachment plate, which serves for the radial adjustment of the mounting bracket as opposed to the one implant part, and that means for the radial fixation of the base plate are associated with the one implant part.

This implant is characterized in that the spacing between the vertebra attachment plate and the center of the implant part can be adjusted, thus enabling a different placement of the implant between the vertebrae, without having to make do without the mounting bracket. The advantage of the greater variability is combined with the advantage of improved stability, since any radial position of the vertebrae attachment plate of the mounting bracket relative to the implant part can be fixed by the means for the radial fixation of the base plate. It is particularly preferred within the scope of the invention, if one mounting bracket is associated with each of the two implant parts, since an even greater stability can be achieved in this manner.

It has further proven advantageous, if the implant part comprises an end plate having a hole facing the adjacent vertebra for receiving the fixing means engaging the base plate, since any limitation as to the circumference of the implant part to the connection to the mounting bracket can be overcome in this manner. It is advantageous with regard to the simplicity of the construction and ease of handling by the surgeon, if the hole is is configured as a threaded bore, and the fixing means is configured as a retaining screw.

A good guidance of the base plate as opposed to the end plate is ensured when the base plate is fork-shaped with at least two fork arms, between which the means for fixation engages. To this end it is also possible, of course, to provide more than two fork arms such that the means for fixation can also interact with different pairs of fork arms in the sense of increased variability, e.g. that the mounting bracket can be adjusted with regard to its lateral alignment relative to the implant part.

A particularly firm connection is achieved when the fork arms have holding ridges beneath the screw head of the retaining screw.

Improved adjustment to anatomical conditions are achieved in that the vertebra attachment plates have a convex cross-sectional shape, at least one screw hole, and a window in the region of the connection to the base plate. To this end the screw hole serves to receive a bone screw, particularly an expansion bolt, by means of which additional securing of the mounting bracket as opposed to the vertebra is achieved. The window in the mounting bracket mainly serves to enable optical control in the region behind the vertebra attachment plate.

In order to obtain an improved mechanical connection between the vertebra and the implant, the base plate comprises at least one anchor barb on the side facing the adjacent vertebra.

It is further particularly preferred within the scope of the invention, if the first implant part and the second implant part are formed as tubular sleeves, that a rotatable threaded ring having teeth is associated with the first implant part, which engages together with a ring thread into a thread arranged in the second implant part, and that a threaded bore is formed in the walls of the first implant for inserting a surgical instrument serving for rotating the threaded ring. The embodiment and the interaction of such first and second implant parts with a surgical instrument is generally known from EP 1 219 266 [U.S. Pat. No. 6,752,832], wherein the implant described therein, and not further explained herein, is suitable for the embodiment according to the invention utilizing the radially adjustable mounting bracket, thus overall enabling a minimally invasive procedure.

In order not to have to fix the mounting bracket as opposed to the implant part according to the analyses of the anatomic conditions ex situ before surgery, it is possible that tool fittings are formed on the screw head for rotating the retaining screw such that access is possible through the window on the screw head, and the retaining screw can also be further tightened in situ. To this end it is of advantage that the window and the threaded bore can be adjusted facing the same side.

It has proven advantageous, if seats are formed between the base plate and the end plate, enabling a primary fixation of location of the mounting bracket as opposed to the implant part before the final fixation of location is carried out by means of tightening the retaining screw. To this end, the seats are advantageously formed by ridges extending transverse to the radial adjustment direction of the guide rail.

BRIEF DESCRIPTION OF THE DRAWING

The invention is further explained in detail based on an illustrated embodiment illustrated in the drawings. Therein.

DETAILED DESCRIPTION

Figure 1:
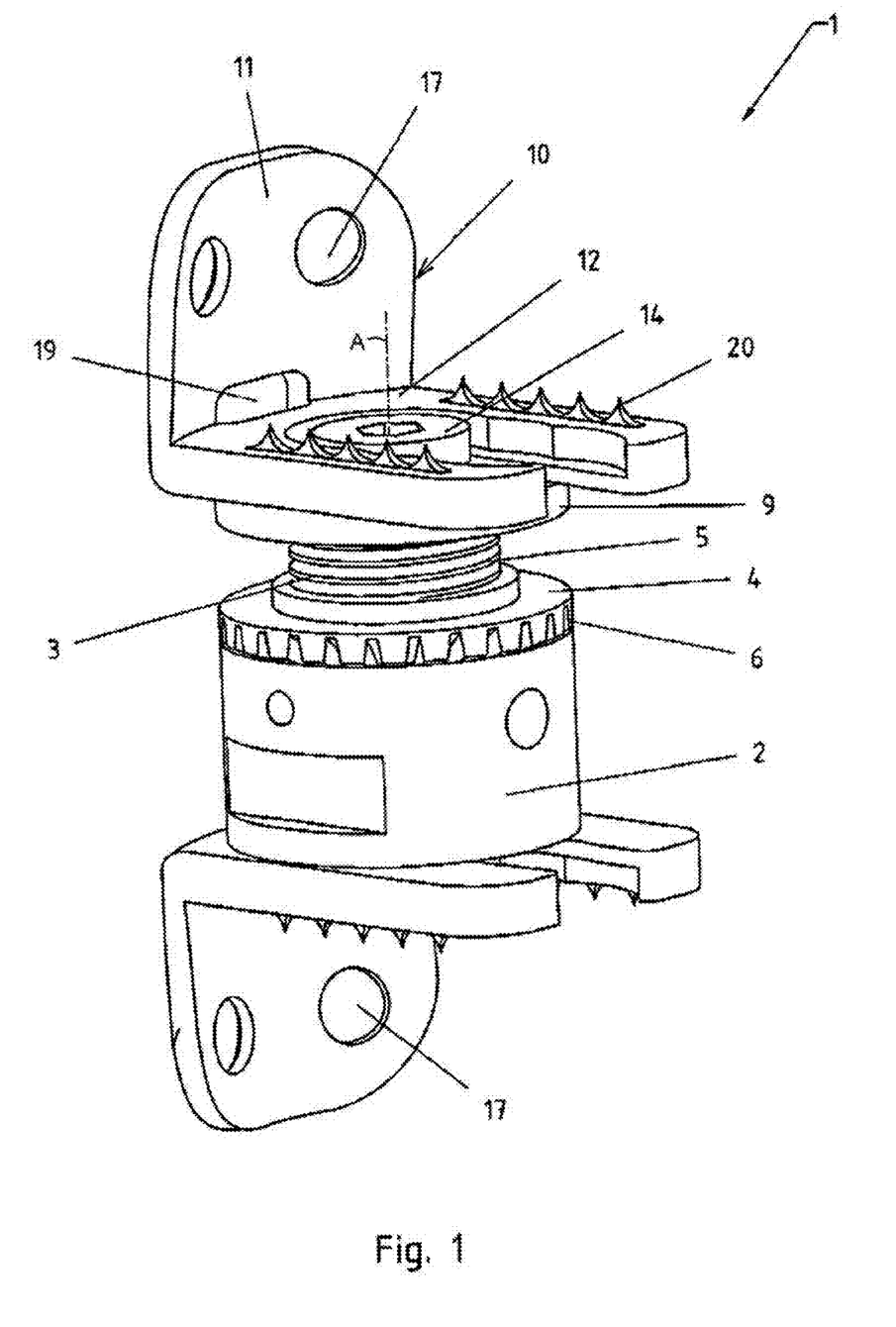
FIG. 1 is a schematic view of an implant according to the invention with two mounting brackets.

FIG. 1 shows an implant 1 for use between vertebrae 8 of the spine as placeholders for vertebrae or vertebral parts removed from the spine. This implant 1 consists of a first implant part 2 and a second implant part 3 that can be moved relative to each other in the direction of their coaxial longitudinal axes for changing the length of the implant 1. This adjustability is achieved in that the first implant part 2 and the second implant part 3 are formed as tubular sleeves, the first implant part 2 surrounding the second implant part 3 and having a rotatable threaded ring 4 carried on the first implant part 2 and having an annular screwthread on its inner edge by means of which it engages into a screwthread 5 of the second implant part 3. The threaded ring 4 is equipped with teeth 6, particularly pinion teeth, on its is outer surface such that the change of length can be achieved for distraction of the vertebrae 8 by rotation of the threaded ring 4 by means of a surgical instrument so as to be screwed into a threaded bore of the first implant part 2.

Figure 4:
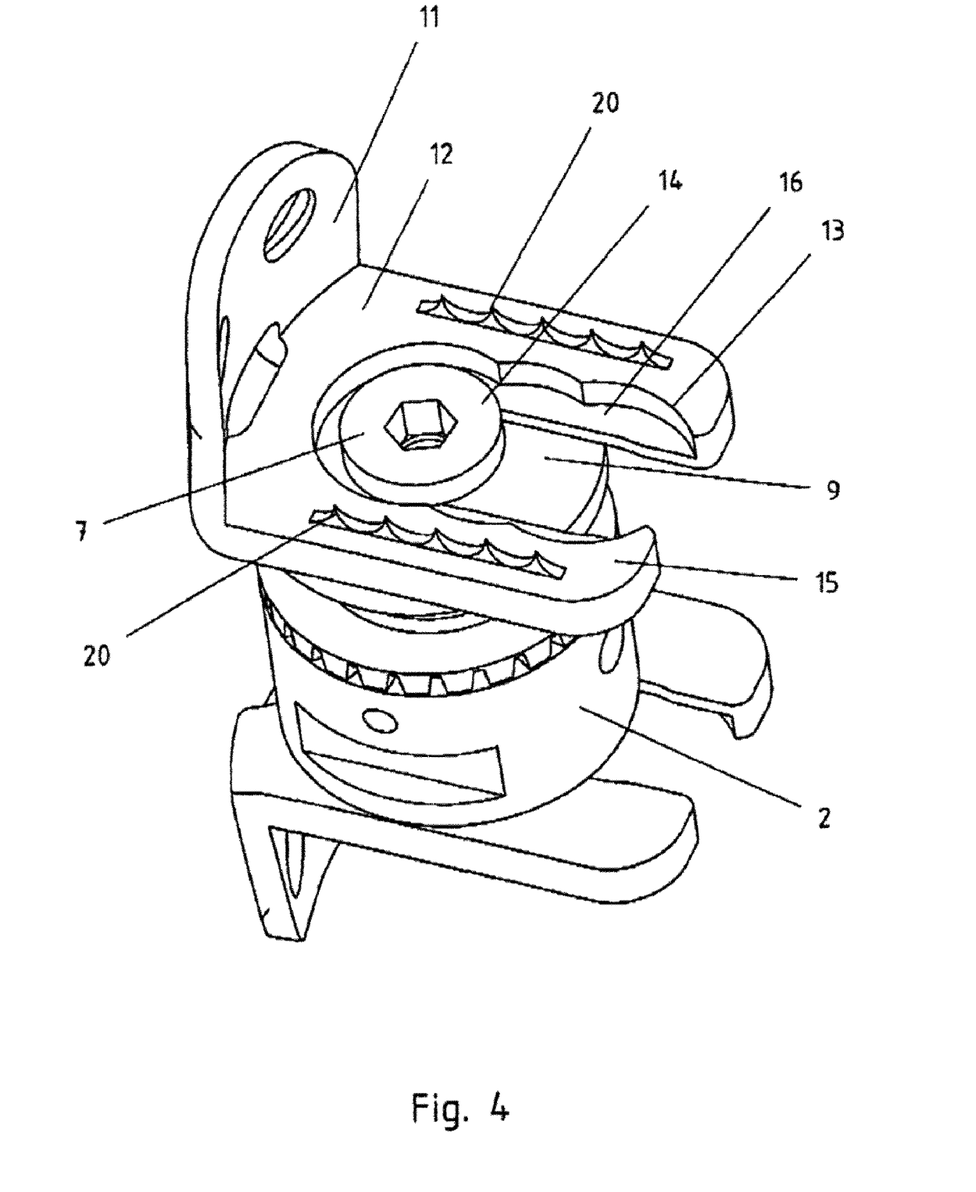
FIG. 4 is a perspective view of the implant of FIG. 3, from a different view.
Figure 5:
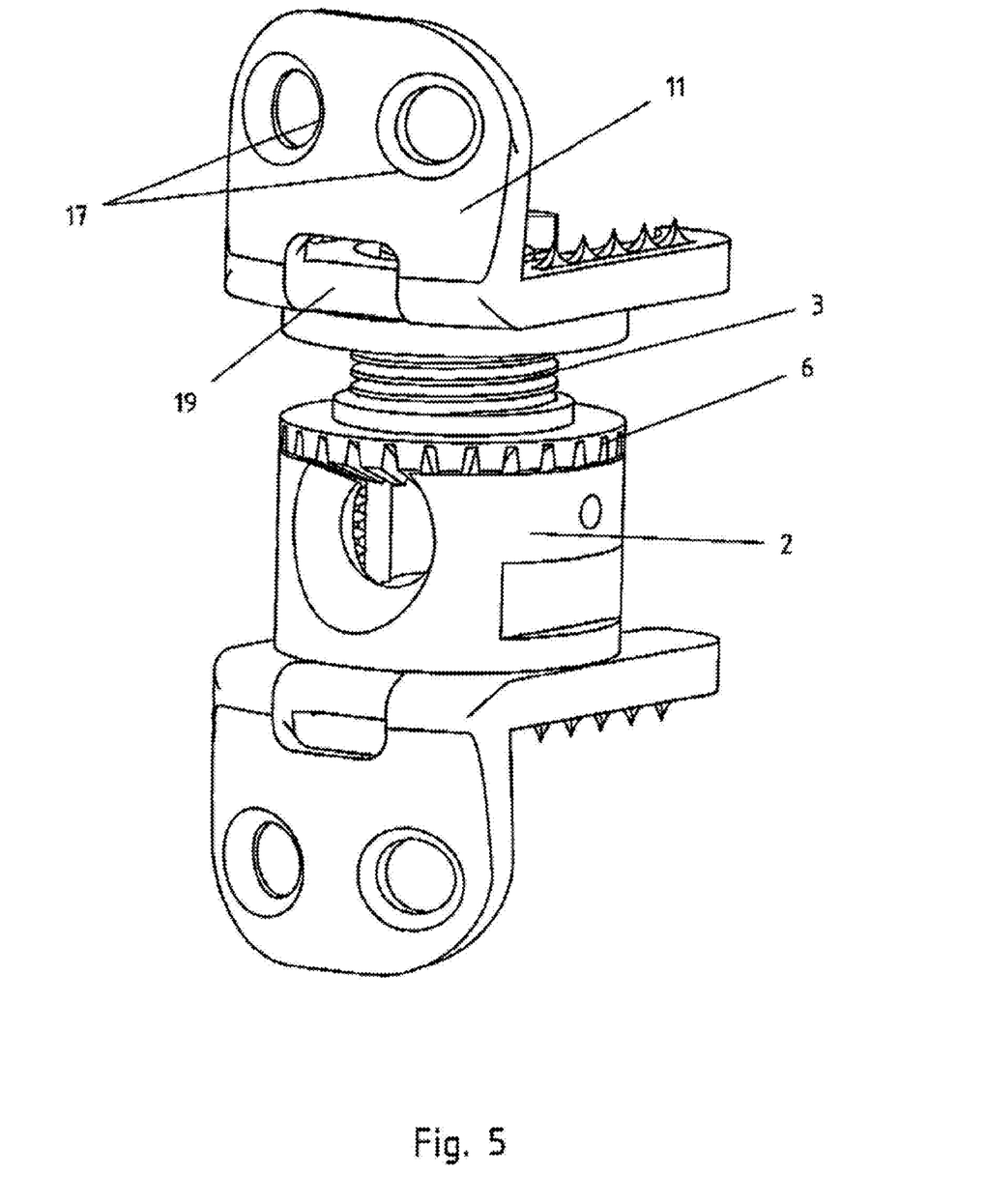
FIG. 5 is a lateral side view of the implant of FIG. 4.
Figure 6:
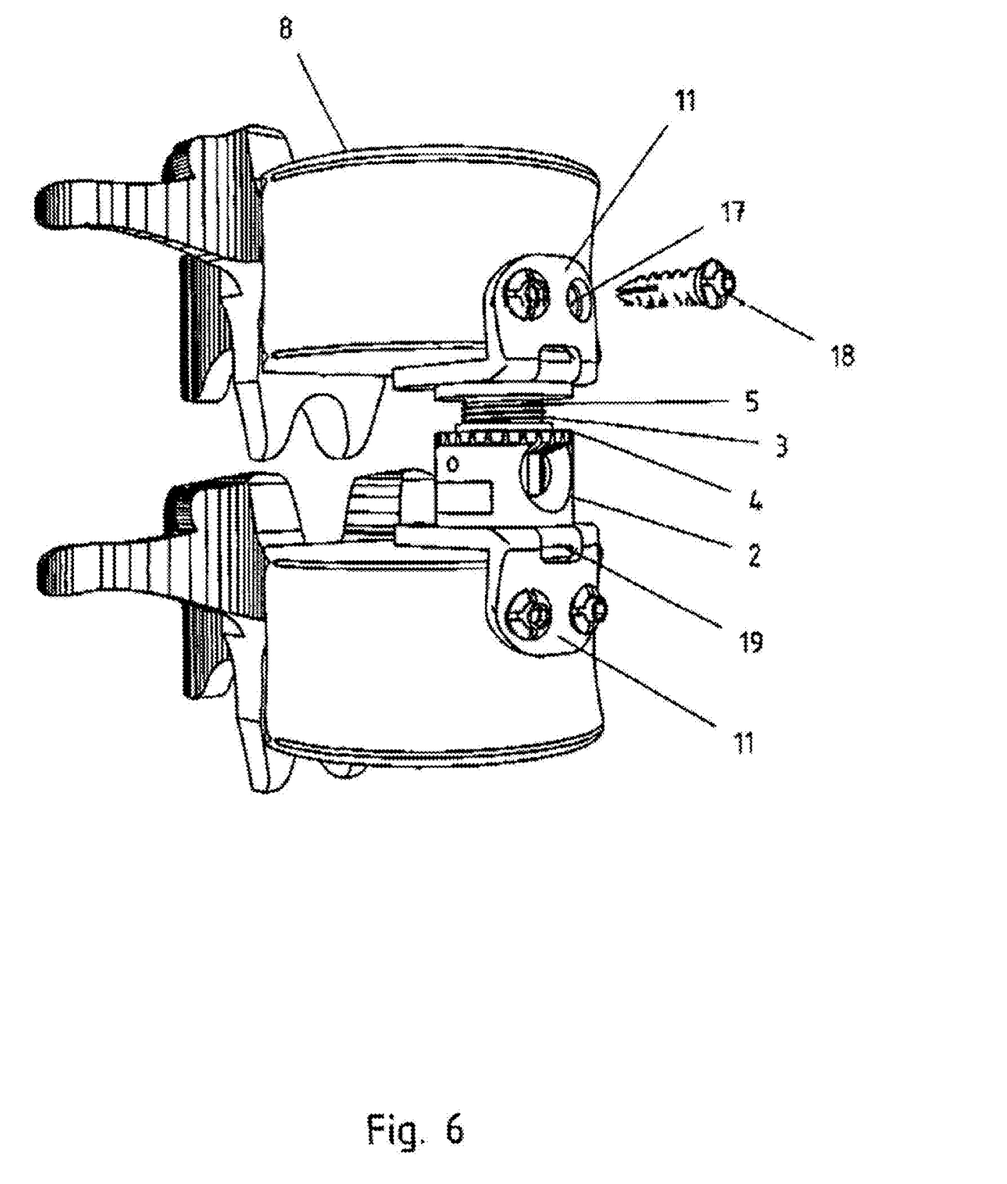
FIG. 6 is a side view of the implant according to the invention installed between two spinal vertebrae.
Figure 7:
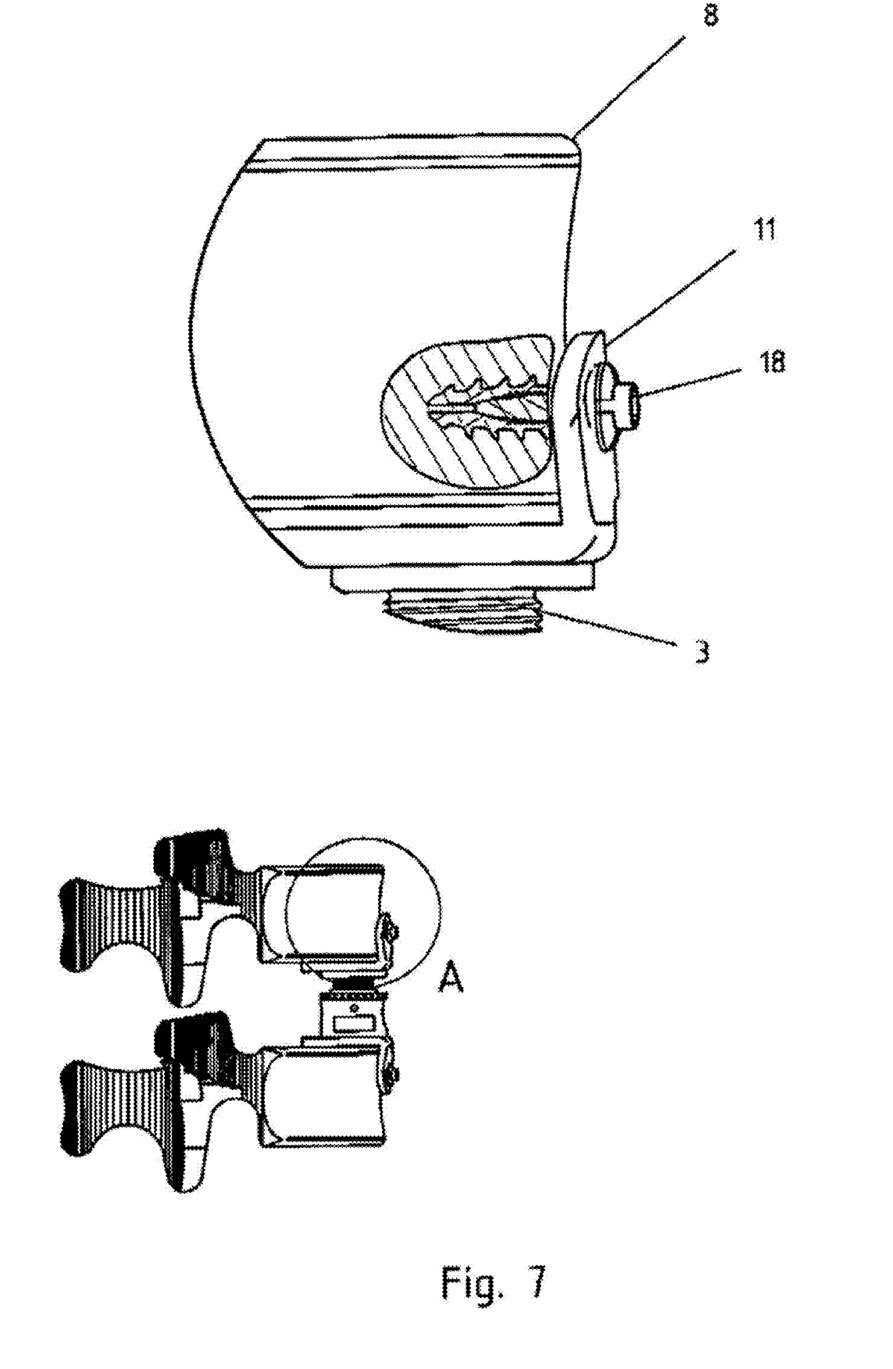
FIG. 7 is detail VII of FIG. 6.

These implant parts 2 and 3 each have an end plate 9 formed with a hole and facing the adjacent vertebra. This end plate 9 is used for releasable attachment to a mounting bracket 10 facing the adjacent vertebra, at least partially covering same, and formed by a vertebra attachment plate 11 and a base plate 12 forming a guide rail 13 projecting from the end plate and serving for the radial positioning of the mounting bracket 10 relative to the implant parts 2 and 3. In the embodiment illustrated in FIG. 1 and FIG. 6, a respective such mounting bracket 10 is associated with each of the two implant parts 2 and 3 and can be fixed to the respective implant part 2 and 3 via a fixing means of the base plate 12, this means being formed in the illustrated embodiment as a retaining screw 14 to be screwed into the hole of the end plate 9 that is formed as a threaded bore. As can be seen in FIG. 4, the base plate 12 is fork-shaped with two arms 15 between which the retaining screw 14 engages, in that it engages holding ridges 16 fitting underneath the screw head 7 of the retaining screw 14. Of course, as an alternative, it is also conceivable as a kinematic reversal to equip the base plates 12 with a bar that is inserted between the fork arms of the end plate 9, like a dovetail guide. In order to adjust the vertebra attachment plate 11 to the curvature of the vertebra 8, it has a convex cross-section, and further has screw holes 17 through which can engage bone screws 18. FIG. 5 shows that the vertebra attachment plate 11 has a window 19 in the region of connection with the base plate 12, allowing access to the region behind the vertebra attachment plate 11 and simultaneously providing the possibility of guiding a tool or instrument through the aperture 19.

Figure 2:
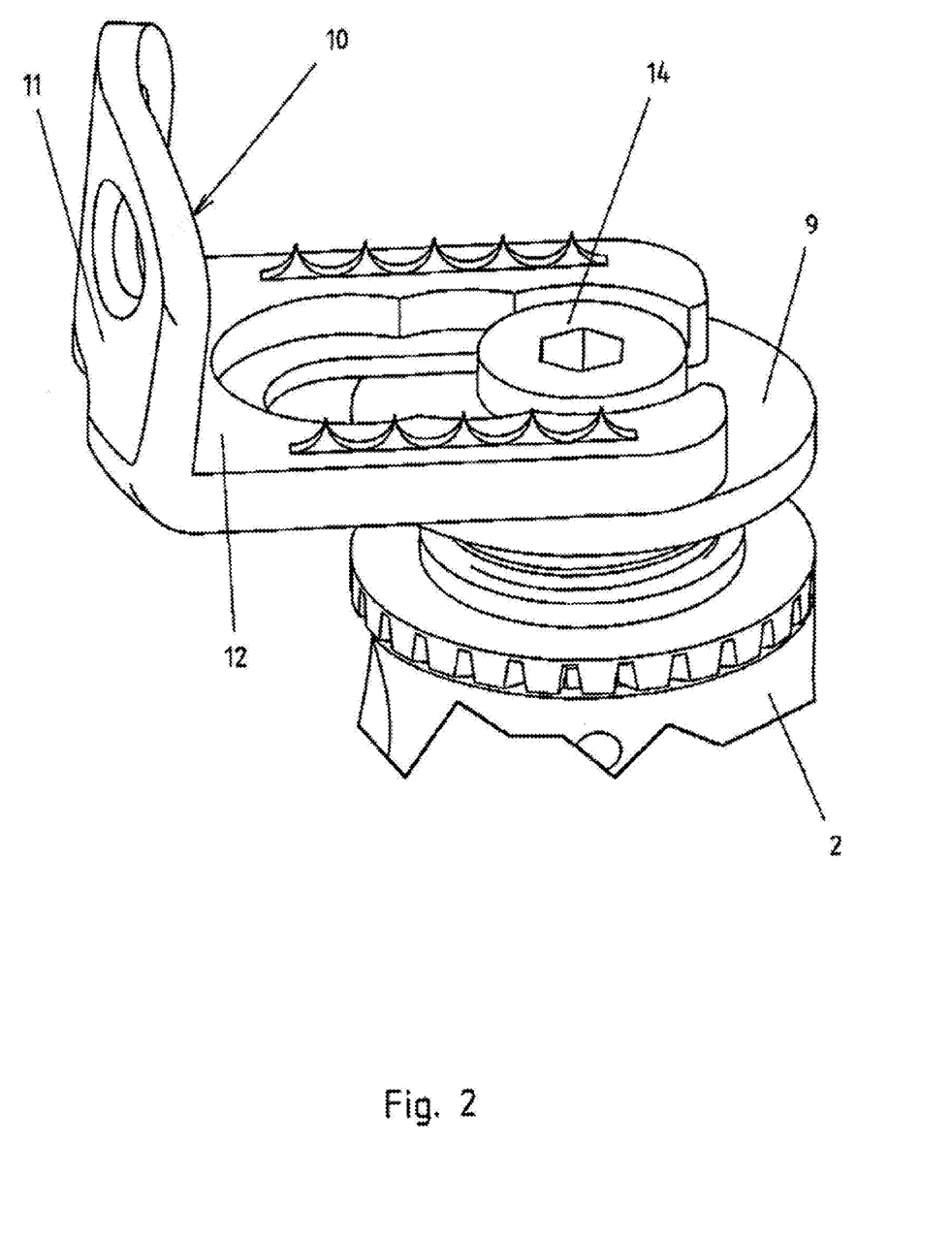
FIG. 2 is a perspective view of the upper part of the implant with its mounting bracket in a first radial position.
Figure 3:
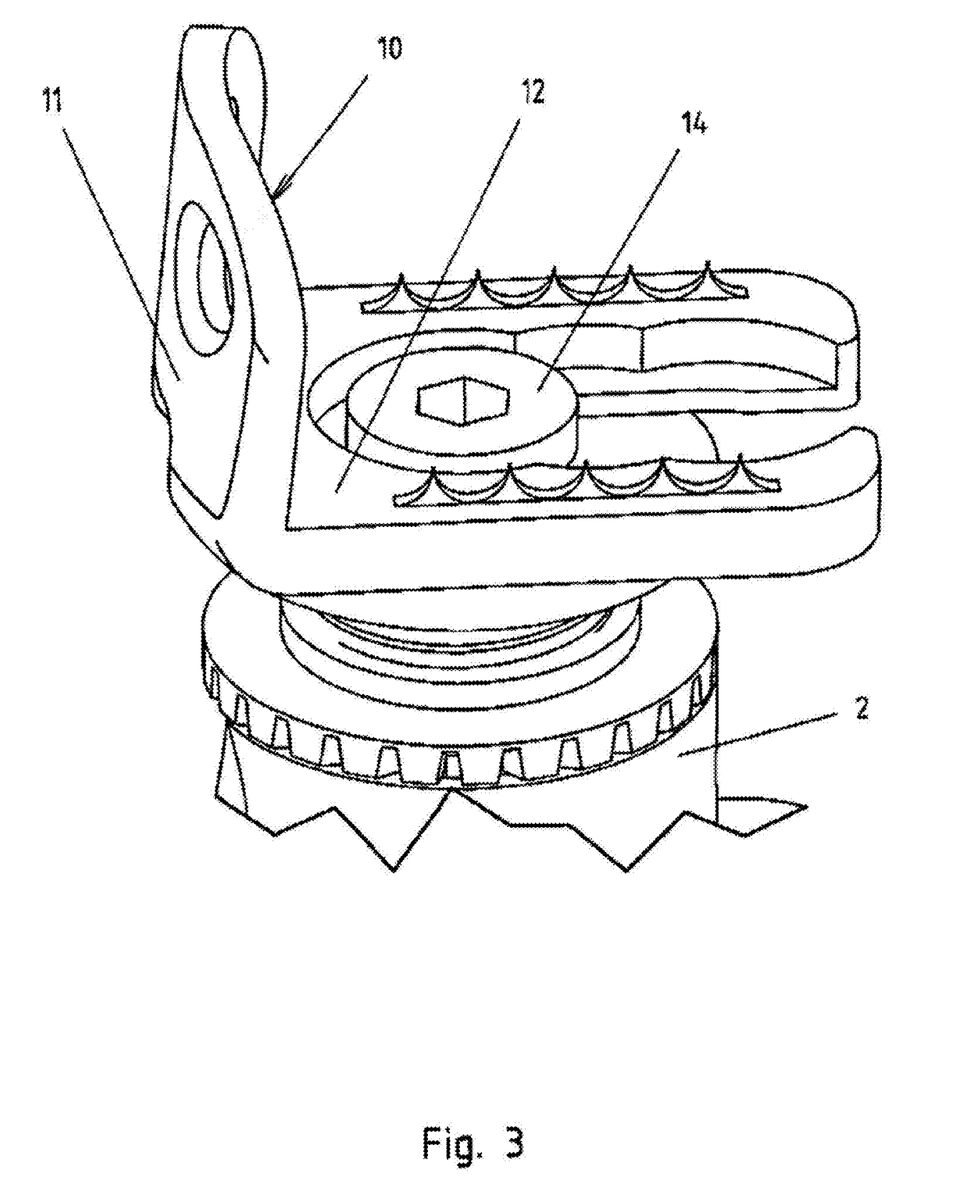
FIG. 3 is a perspective view of the upper part of the implant with its mounting bracket in a second radial position.

As shown particularly in FIGS. 2 to 4, the base plate 12 has on its side facing the adjacent vertebra a plurality of anchor barbs 20 that can penetrate the vertebra 8, thus bringing about a fixation of location before bone screws 18, preferably expansion bolts, are inserted through the screw holes 17.

In order to utilize the implant 1 according to the invention, the required position of the mounting bracket 10 relative to the implant parts 2 and 3 is carefully determined by means of an imaging method as preparation of the surgery, and the mounting bracket 10 is solidly mounted to the implant part 2 and 3. During surgery, distraction of the implant 1 can then be carried out by means of a surgical instrument inserted into the threaded bore for achieving the necessary height in order to subsequently carry out the final fixation of the implant 1 by means of the bone screws 18, resulting in a very stable connection, whereby particularly the angular stability thereof, which is achieved by the bone screws 18, should be noted.

If a fixation of the position of the mounting bracket 10 as opposed to the implant part 2 and 3 ex situ is not possible, the actuation of the retaining screw 14 is impeded, since it is not accessible an axial end because it is blocked by the vertebra 8. Actuation still remains possible by access through the window 19. According to the illustrated embodiment not illustrated in the drawing, the invention provides for this in that seats are formed between the base plate 12 and the end plate 9 by means of formations extending transverse to the radial adjustment direction of the guide rail 13.

The invention claimed is:

1. An implant for use between a pair of spinal vertebrae, the implant comprising:
    first and second center parts formed as tubular sleeves and extending along an axis, the second center part having an external screwthread and the first center part having a radially open bore;
    a threaded ring with teeth on the first center part, threaded onto the second center part, and rotatable to change an overall axial length of the center parts, the first center part being formed with a bore for inserting a surgical instrument serving for rotating the threaded ring;
    respective first and second brackets each having an attachment plate fixable to a respective one of the vertebrae and a base plate connected to the respective center part, each attachment plate being of convex cross-section and being formed with at least one screw hole and with a respective window adjacent the respective base plate, the window and the bore on the side of the first center part being orientable to face radially in the same direction;
    an end plate on the first center part having a threaded bore and bearing axially on the base plate of the first bracket;
    a guide between the base plate of the first bracket and the first center part for radial shifting the first center part on the base plate of the first bracket; and
    a retaining screw engaged through the base plate of the first bracket and into the threaded bore of the end plate for fixing any of a plurality of radially offset positions of the base plate of the first bracket and the first center part.

2. An implant for use between a pair of spinal vertebrae, the implant comprising:
    first and second center parts extending along an axis;
    formations on the center parts actuatable to change an overall axial length of the center parts;

respective first and second brackets each having an attachment plate fixable to a respective one of the vertebrae and a base plate connected to the respective center part, each attachment plate being of convex cross-section and being formed with at least one screw hole and with a respective window adjacent the respective base plate;

an end plate on the first center part having a threaded bore and bearing axially on the base plate of the first bracket;

seats formed between the base plate and the end plate, the base plate of the first bracket extending radially and the seats being formed by ridges extending transverse to the radial extension direction of the base plate of the first bracket;

a guide between the base plate of the first bracket and the first center part for radial shifting the first center part on the base plate of the first bracket; and a retaining screw engaged through the base plate of the first bracket and into the threaded bore of the end plate for fixing any of a plurality of radially offset positions of the base plate of the first bracket and the first center part.

3. An implant for use between a pair of adjacent spinal vertebrae, the implant comprising:

first and second center parts extending along an axis;

formations on the center parts actuatable to change an overall axial length of the center parts;

respective first and second brackets each having an attachment plate fixable to a respective one of the vertebrae and a base plate connected to the respective center part and each having at least one anchor barb on a side facing a respective one of the adjacent vertebrae, each attachment plate being of convex cross-section and being formed with at least one screw hole and with a respective window adjacent the respective base plate;

an end plate on the first center part having a threaded bore and bearing axially on the base plate of the first bracket;

a guide between the base plate of the first bracket and the first center part for radial shifting the first center part on the base plate of the first bracket; and a retaining screw engaged through the base plate of the first bracket and into the threaded bore of the end plate for fixing any of a plurality of radially offset positions of the base plate of the first bracket and the first center part.

4. The implant according to claim 3 wherein a mounting bracket is associated with each of the two center parts.

5. The implant according to claim 3 wherein the base plate of the first bracket is fork-shaped and has at least two fork arms between which the retaining screw engages.

6. The implant according to claim 5 wherein the fork arms have gripping holding ridges beneath a screw head of the retaining screw.

7. The implant according to claim 5 wherein the base plate is equipped with a ridge for fitting between the fork arms of the base plate of the first bracket.

8. The implant according to claim 3 wherein the first center part and the second center part are formed as tubular sleeves, the formations including a rotating threaded ring with teeth associated with the first center part and engaging with an annular thread into a thread associated with the second center part, and that a bore is formed in the side of the first center part for inserting a surgical instrument serving for rotating the threaded ring.

9. The implant according to claim 3 wherein tool fittings are formed on a head of the retaining screw for rotating the retaining screw by a tool extending through the window.

10. The spinal implant defined in claim 3 wherein each of the brackets is L-shaped and unitarily formed with the respective base plate and attachment plate.

11. The spinal implant defined in claim 10 wherein both of the brackets are provided with one such guide means and retaining screw.

12. An implant for use between a pair of spinal vertebrae, the implant comprising:

first and second center parts extending along an axis;

formations on the center parts actuatable to change an overall axial length of the center parts;

respective first and second brackets each having an attachment plate fixable to a respective one of the vertebrae and a base plate connected to the respective center part, each attachment plate being of convex cross-section and being formed with at least one screw hole and with a respective window adjacent the respective base plate, the first-bracket base plate being forked and having a pair of arms defining a diametrally extending guide slot;

an end plate on the first center part having a threaded bore and bearing axially on the base plate of the first bracket;

a guide between the base plate of the first bracket and the first center part for radial shifting the first center part on the base plate of the first bracket; and a retaining screw engaged through the base plate of the first bracket and into the threaded bore of the end plate and having a head slidable diametrally in the slot for fixing any of a plurality of radially offset positions of the base plate of the first bracket and the first center part, the guide having undercut edges forming recessed ridges on which the head of the retaining screw bears axially, a top face of the head being level with or below a top face of the base plate of the first bracket.

\* \* \* \* \*